United States Patent [19]

Darms

[11] 4,196,144
[45] Apr. 1, 1980

[54] AROMATIC DIAMINES AND THEIR USE AS POLYCONDENSATION COMPONENTS FOR THE MANUFACTURE OF POLYAMIDE, POLYAMIDE-IMIDE AND POLYIMIDE POLYMERS

[75] Inventor: Roland Darms, Therwil, Switzerland

[73] Assignee: Ciba-Geigy Corporation, Ardsley, N.Y.

[21] Appl. No.: 963,058

[22] Filed: Nov. 22, 1978

Related U.S. Application Data

[63] Continuation of Ser. No. 802,922, Jun. 2, 1977, abandoned.

[30] Foreign Application Priority Data

Jun. 15, 1976 [CH] Switzerland ................ 7593/76

[51] Int. Cl.$^2$ ................................ C07C 93/06
[52] U.S. Cl. ................................ 260/571; 528/28; 528/125; 528/126; 528/172; 528/179; 528/180; 528/185
[58] Field of Search .............. 260/574, 571, 180, 177

[56] References Cited

U.S. PATENT DOCUMENTS

| | | | |
|---|---|---|---|
| 3,140,316 | 7/1964 | Towle | 260/580 |
| 3,410,875 | 11/1968 | Holub | 260/346.3 |
| 3,440,215 | 4/1969 | Holub | 260/47 |
| 3,505,288 | 4/1970 | Bodesheim et al. | 260/47 |
| 3,699,075 | 10/1972 | Lubowitz | 260/49 |
| 3,705,869 | 12/1972 | Darmory et al. | 260/30.2 R |
| 3,748,338 | 7/1973 | Darmory et al. | 260/30.2 R |
| 3,755,449 | 8/1973 | Ito et al. | 260/571 |
| 3,758,434 | 9/1973 | Kunzel et al. | 260/30.2 |

FOREIGN PATENT DOCUMENTS

| | | | |
|---|---|---|---|
| 1537385 | 7/1968 | France | 260/571 |
| 1560940 | 3/1969 | France | 260/571 |
| 1030026 | 5/1966 | United Kingdom | 260/578 |

OTHER PUBLICATIONS

Arcoria et al., "Chem. Ab.", Ab. No. 31031u (1968).

Primary Examiner—John Doll
Attorney, Agent, or Firm—Luther A. R. Hall

[57] ABSTRACT

New polynuclear aromatic diamines, such as 2,2'-di-(p-aminophenoxy)-biphenyl, a process for their manufacture and their use as polycondensation components for the manufacture of polyamide, polyamide-imide and polyimide polymers are described. The polymers obtained with the aromatic diamines according to the invention are readily soluble and can also be processed from the melt and are distinguished by good thermal, electrical and/or mechanical properties.

5 Claims, No Drawings

AROMATIC DIAMINES AND THEIR USE AS POLYCONDENSATION COMPONENTS FOR THE MANUFACTURE OF POLYAMIDE, POLYAMIDE-IMIDE AND POLYIMIDE POLYMERS

This is continuation of application Ser. No. 802,922, filed on June 2, 1977, now abandoned.

The present invention relates to new aromatic diamines, a process for their manufacture and their use as polycondensation components for the manufacture of polyamide, polyamideimide and polyimide polymers.

It is known that, in general, polyamides, polyamideimides and polyimides, and above all aromatic polymers of this type, can be processed only with difficulty. It is also known that the solubility of such polymers can be somewhat improved if bulky diamines or dianhydrides containing 3 or more aromatic rings are used for their manufacture (compare, for example, DT-AS 1,595,733 and DT-OS 2,009,739, 2,153,829, 2,257,996 and 2,321,513). However, these polymers have the disadvantage that they cannot be processed from the melt, or can be processed from the melt only with difficulty. Moreover, the stability to heat and/or chemical stability of these polymers is inadequate in some cases.

The object of the invention was, therefore, to provide polymers which are readily soluble and can also be processed from the melt, without this resulting in a deterioration in the chemical, thermal, electrical and mechanical properties of the polymers.

It has been found that polyamides, polyamide-amide-acids and polyamide-acids, and corresponding cyclised (imidised) derivatives, which are readily soluble and can be processed easily and have excellent thermal, electrical and/or mechanical properties can be manufactured by using new aromatic diamines.

The new diamines correspond to the formula I

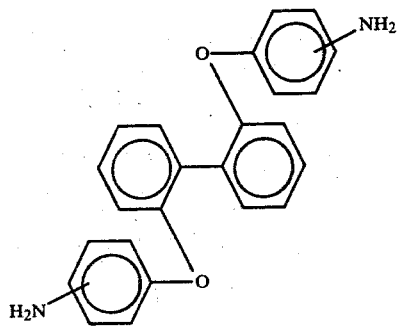

(I), in which the amino groups independently of one another are in the o-, m- or p-position of the benzene ring.

Symmetrical diamines of the formula I, that is to say those in which the amino groups are each in the same position of the benzene ring, and above all the diamines of the formula I in which the two amino groups are each in the ortho-position or in the para-position of the benzene ring are preferred.

The new diamines of the formula I can be manufactured, for example, by either reacting a compound of the formula IIa

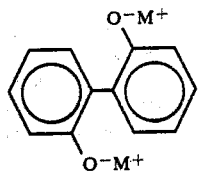

(IIa), in a molar ratio of at least 1:2 with a compound of the formula IIIa

(IIIa)

or reacting a compound of the formula IIb

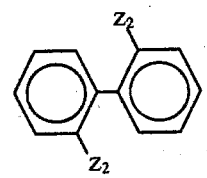

(IIb)

in a molar ratio of at least 1:2 with a compound of the formula IIIb

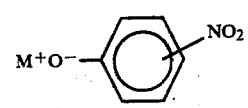

(IIIb), in which M denotes a hydrogen, alkaline earth metal or alkali metal cation, a trialkyl-ammonium cation with 3–24, and especially 3–12, carbon atoms, or a quaternary ammonium cation, $Z_1$ denotes a halogen atom or, if the nitro group is in the ortho-position relative to $Z_1$, also denotes a nitro group and $Z_2$ denotes a halogen atom, to give a compound of the formula IV

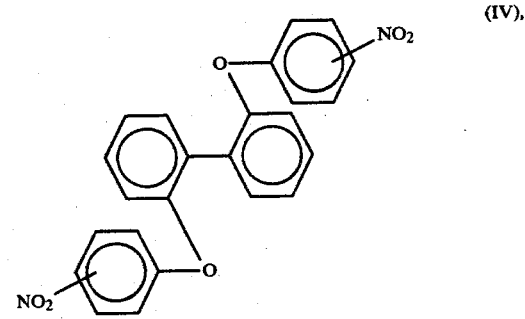

(IV), in which the two nitro groups independently of one another are in the o-, m- or p-position of the benzene ring, and subsequently converting the compound of the formula IV into a compound of the formula I.

Mixtures of two different compounds of the formula IIIa or IIIb can also be used in the above process.

Possible halogen atoms $Z_1$ and $Z_2$ are bromine atoms, but especially chlorine atoms and fluorine atoms.

If M represents an alkaline earth metal cation or an alkali metal cation, this cation is, for example, the Ba, Mg, Ca, Li, Na or K cation. Examples of suitable trialkyl-ammonium cations M are the trimethyl-ammonium, triethyl-ammonium, methyldiethyl-ammonium and tri-n-octyl-ammonium cation, whilst possible quaternary ammonium cations are, for example, the benzyltrimethyl-ammonium cation and the tetramethyl-ammonium cation. M preferably represents the hydrogen, Na or K cation.

The reaction of the compounds of the formula IIa and IIb with the compounds of the formula IIIa and IIIb can be carried out in an aqueous-organic or organic medium or, alternatively, in the melt.

If M in formula IIa or IIIb represents hydrogen, the reaction is advantageously carried out in an aqueous-organic or organic medium and optionally in the presence of an acid-binding agent. Examples of acid-binding agents which can be used are inorganic and organic bases, such as alkaline earth metal hydroxides and carbonates and alkali metal hydroxides and carbonates, especially the hydroxides or carbonates of Na or K, and tertiary amines, such as triethylamine, pyridine or pyridine bases.

The inert organic solvents used are, appropriately, polar aprotic solvents, for example dialkylsulphoxides, such as dimethylsulphoxide and diethylsulphoxide, tetramethylenesulphone or dimethylsulphone.

Compounds of the formula IIa and IIIb in which M represents an alkaline earth metal cation, an alkali metal cation, a trialkyl-ammonium cation or a quaternary ammonium cation are preferred for the reaction in the melt.

The reaction temperatures are generally between about 50° C. and 150° C. for the reaction in an organic or aqueous-organic medium and between about 100° C. and 200° C., preferably between about 130° C. and 160° C., for the reaction in the melt.

Compounds of the formula IIb and IIIb, but especially compounds of the formula IIa and IIIa in which M represents the hydrogen cation or an alkali metal cation, especially the sodium cation or potassium cation, and $Z_1$ and $Z_2$ represent chlorine or fluorine are preferably used.

The compounds of the formulae IIa, IIb, IIIa and IIIb are preferably employed in stoichiometric amounts. However, the reaction can also be carried out with a slight excess of one or the other reactant.

The reduction (hydrogenation) of the compounds of the formula IV can be carried out in a manner which is in itself known, for example with iron in an acid medium by the Béchamp method, optionally in the presence of neutral salts, such as iron-II sulphate, $CaCl_2$ or sodium hydrogen sulphate; with tin or tin-II chloride in the presence of HCl; with zinc in an acid or neutral medium, optionally with the addition of neutral salts, such as $CaCl_2$ and $NH_4Cl$; with lithium aluminium hydride; with hydrazines, such as hydrazine hydrate and phenylhydrazine, if necessary with the addition of Raney nickel catalysts, and with sodium dithionite ($Na_2S_2O_4$).

Catalytic reduction is preferred. Examples of suitable catalysts are palladium, palladium-on-charcoal, platinum, platinum black, platinum oxide and, above all, Raney nickel. The catalytic reduction is appropriately carried out in a suitable inert organic solvent, such as dioxane or methylcellosolve.

According to a further process, diamines, according to the invention, of the formula I can, according to the Ullmann reaction, also be manufactured by heating a compound of the formula V

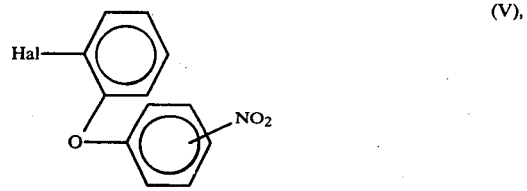

in which Hal denotes fluorine, chlorine, bromine or iodine, in the presence of copper-bronze and subsequently hydrogenating the resulting compound of the formula IV. The reaction can be carried out in a suitable high-boiling organic solvent, such as diphenyl ether or trimethylene glycol dimethyl ether. However, the reaction in the melt is preferred.

Finally, diamines of the formula I can also be obtained by reacting a biphenyl dihalide of the formula IIb with a compound of the formula IIIc

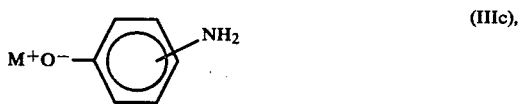

in which what has been stated above applies in respect of M.

The compounds of the formulae IIa, IIb, IIIa, IIIb and IIIc are known or can be manufactured easily in a manner which is in itself known. The compounds of the formula V can be obtained, for example, by reacting nitrochlorophenols with, for example, ortho-bromophenolates or by halogenating nitrodiphenyl ethers.

The compounds of the formula IV are also new. Both these compounds and the diamines of the formula I can, after the reaction, be isolated, and purified, in a customary manner, for example by washing with water or diethyl ether or by filtering and recrystallising from suitable solvents, such as methanol or ethanol. The compounds of the formula I and IV are obtained in the form of white to slightly yellowish crystals.

The diamines according to the invention can be used as polycondensation components for the manufacture of polyamide, polyamide-imide and polyimide homopolymers or copolymers. The present invention therefore also relates to new polyamides, polyamide-amide-acids or polyamide-acids which consist of 1 to 100 mol% of structural elements of the formula VI

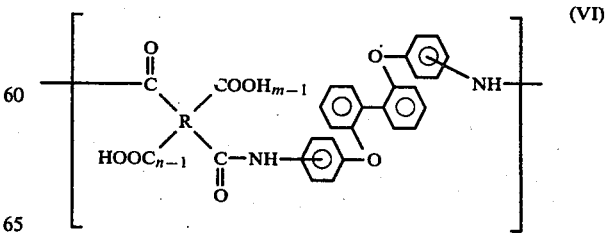

and of 0 to 99 mol% of structural elements of the formula VII

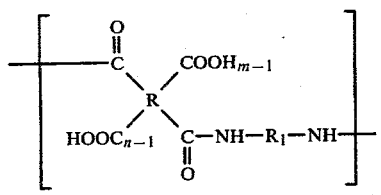

in which the NH groups in formula VI independently of one another are bonded to the benzene nucleus in the o-, m- or p-position and the individual m, n, R and $R_1$ independently of one another have the following meanings: m and n denote the number 1 or 2, R denotes an aliphatic radical with at least two carbon atoms or a cycloaliphatic, carbocyclic-aromatic or heterocyclic-aromatic radical, the carbonamide groups and carboxyl groups being bonded to different carbon atoms and, if R denotes a cyclic radical and at least one of m and n denotes the number 2, the carboxyl groups each being in the ortho-position relative to a carbonamide group, and $R_1$ denotes an aliphatic radical with at least two carbon atoms or a cycloaliphatic, araliphatic, carbocyclic-aromatic or heterocyclic-aromatic radical, and also to the corresponding derivatives which have been cyclised to the imide.

These polyamides, polyamide-amide-acids or polyamide-acids and the corresponding derivatives which have been cyclised to the imide can be manufactured by subjecting 1–100 mol% of a diamine of the formula I

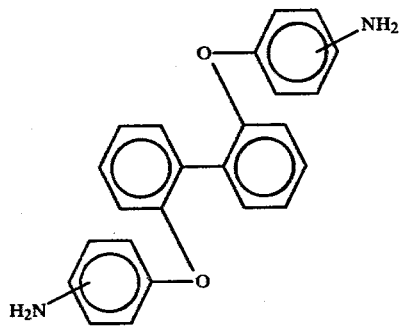

in which the NH$_2$ groups independently of one another are in the o-, m- or p-position of the benzene nucleus, and 0–99 mol% of a diamine of the formula VIII

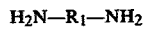

to a condensation reaction with essentially stoichiometric amounts of a compound of the formula IX

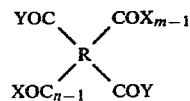

in which what has been stated under formulae VI and VII applies in respect of m, n, R and $R_1$ and, when m and/or n=2, X, together with Y, forms the —O— grouping and Y represents a chlorine atom, a hydroxyl group, an unsubstituted or substituted phenoxy group or an alkoxy group with 1–18, and especially 1–12, carbon atoms, or, if m and/or n=2, Y, together with X, forms the —O— grouping, the groups —COY and —COX being bonded to different carbon atoms and, if R represents a cyclic radical and m and/or n=2, the —COY group or groups being in the ortho-position relative to a —COX group, and optionally subsequently cyclising the resulting polymers, in which m and/or n=2, to the imide.

The polyamides, polyamide-amide-acids and polyamide-acids according to the invention in general have an intrinsic viscosity in N,N-dimethylacetamide (DMA) at 25° C. of about 0.04 to 4.0 dl/g and especially of 0.1 to 2.5 dl/g. The intrinsic viscosity of the cyclised derivatives, that is to say the polyamide-imides and polyimides, in concentrated H$_2$SO$_4$ or DMA at 25° C. is of the same order of size.

The intrinsic viscosity $\eta_{intrinsic}$ is calculated according to the following equation $$\eta\ intrinsic = \frac{\ln \frac{\eta}{\eta_o}}{c}.$$

In this equation: ln denotes the natural logarithm, $\eta$ denotes the viscosity of the solution (0.5% by weight of the polymer in suitable solvents, preferably N,N-dimethylacetamide or concentrated sulphuric acid), $\eta_o$ denotes the viscosity of the solvent and c denotes the concentration of the polymer solution in g of polymer/100 ml of solvent.

The viscosity measurements are carried out at 25° C.

The polymers according to the invention can be homopolymers or copolymers which have statistical distribution of the individual structural elements of the formulae VI and VII. In the individual structural elements, the m, n, R and $R_1$ can also have different meanings. However, the polymers can also be homopolymers or copolymers which have any desired, and at least in part a block-like arrangement of polyamide, polyamide-amide-acid or polyamide-acid structural elements, according to the definition, of the formulae VI and VII. Hompolymers or copolymers of this type can be obtained, for example, by first allowing a diamine of the formula I to react with a slight excess of a specific di-, tri- or tetra-carboxylic acid derivative of the formula IX, for example with a dicarboxylic acid derivative, and then adding another di-, tri- or tetra-carboxylic acid derivative of the formula IX, a diamine of the formula VIII and/or further diamine of the formula I to the reaction mixture.

An additional advantage of the invention is that it is, in general, already possible to manufacture copolymers which have the desired improved properties by the addition of relatively small amounts of diamine of the formula I.

Preferably, the individual m, n, R, $R_1$, X and Y have the same meaning and the NH and NH$_2$ groups in formula VI and I respectively are both in the same position, especially in the o-position and above all in the p-position of the benzene ring.

According to a further preference, the polyamides, polyamide-amide-acids or polyamide-acids according to the invention, and the corresponding cyclised derivatives, consist only of structural elements of the formula VI. However, polymers, according to the definition, which consist of 5–80 mol% of structural elements of the formula VI and of 20–95 mol% of structural elements of the formula VII, and the corresponding cyclised derivatives, are particularly preferred.

If Y represents a substituted phenoxy group, these groups are, in particular, phenoxy groups substituted by nitro groups or alkyl or alkoxy groups with 1 or 2 carbon atoms or by halogen atoms, above all chlorine or fluorine, such as the 2-, 3- or 4-nitrophenoxy group, 2,4- or 3,5-dinitrophenoxy group or 3,5-dichlorophenoxy group or the pentachlorophenoxy, 2-methylphenoxy or 2-methoxyphenoxy group.

Alkoxy groups Y can be straight-chain or branched. Examples which may be mentioned are: the methoxy, ethoxy, n-propoxy, isopropoxy, n-butoxy, tert.-butoxy, hexyloxy, octoxy, decyloxy, dodecyloxy, tetradecyloxy and octadecyloxy group. Unsubstituted phenoxy groups or alkoxy groups with 1–12, and especially 1–4, carbon atoms are preferred.

If R represents an aliphatic radical, these radicals are, preferably, unsubstituted, straight-chain or branched alkylene groups with 2–10 carbon atoms.

Cycloaliphatic radicals represented by R are, above all, 5-membered or 6-membered cycloalkylene groups.

If R denotes a carbocyclic-aromatic radical, this preferably contains at least one 6-membered ring; such radicals are, in particular, monocyclic radicals, fused polycyclic radicals or polycyclic radicals which have several cyclic, fused or non-fused systems which can be linked to one another direct or via bridge members. Examples of suitable bridge members which may be mentioned are —O—, —CH$_2$CH$_2$—, —CH$_2$—,

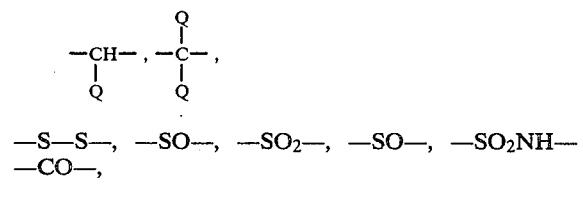

—S—S—, —SO—, —SO$_2$—, —SO—, —SO$_2$NH— —CO—,

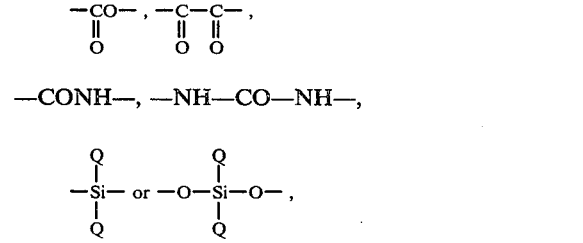

—CONH—, —NH—CO—NH—, $$-\underset{\underset{Q}{|}}{\overset{\overset{Q}{|}}{Si}}-\text{ or }-O-\underset{\underset{Q}{|}}{\overset{\overset{Q}{|}}{Si}}-O-,$$

in which Q denotes an alkyl group with 1–6, and preferably 1–4, carbon atoms or a phenyl group.

If R denotes a heterocyclic-aromatic radical, possible radicals are, in particular, 5-membered or 6-membered heterocyclic-aromatic, optionally benzo-condensed ring systems containing O, N and/or S.

Carbocyclic-aromatic or heterocyclic-aromatic radicals represented by R can also be substituted, for example by nitro groups, alkyl groups with 1–4 carbon atoms, trifluoromethyl groups, halogen atoms, especially chlorine, or silyl, sulphonic acid or sulphamoyl groups.

Aliphatic, araliphatic, cycloaliphatic, carbocyclic-aromatic or heterocyclic-aromatic radicals represented by R$_1$ can be unsubstituted or substituted, for example by halogen atoms, such as fluorine, chlorine or bromine, or by alkyl or alkoxy groups, each with 1–4 carbon atoms.

Possible aliphatic radicals R$_1$ are, above all, straight-chain or branched alkylene groups with 2–12 carbon atoms, it being possible for the alkylene chain also to be interrupted by hetero-atoms, such as O, S or N atoms.

In the meaning of a cycloaliphatic radical, R$_1$ represents, for example, the 1,3- or 1,4-cyclohexylene group, the 1,4-bis-(methylene)-cyclohexane group or the dicyclohexylmethane group, whilst possible araliphatic radicals are, above all, 1,3-, 1,4- or 2,4-bis-alkylenebenzene radicals, 4,4'-bis-alkylene-diphenyl radicals and 4,4'-bis-alkylene-diphenyl ether radicals.

If R$_1$ represents a carbocyclic-aromatic radical, such radicals are, preferably, monocyclic aromatic radicals, fused polycyclic aromatic radicals or non-fused bicyclic aromatic radicals and in the case of the latter the aromatic nuclei are bonded to one another via a bridge member. Possible bridge members are the groups mentioned in the preceding text when discussing R.

If R$_1$ denotes a heterocyclic-aromatic radical, such radicals are, in particular, heterocyclic-aromatic of 5-membered or 6-membered rings containing O, N and/or S. Advantageously, R represents an unsubstituted alkylene group with 4–10 carbon atoms or an unsubstituted monocyclic, a fused bicyclic or a non-fused bicyclic aromatic radical and in the case of the latter the aromatic nuclei are bonded to one another via the bridge member —O—, —CO— or —SO$_2$—, whilst R$_1$ denotes an unsubstituted alkylene group with 2–10 carbon atoms, a bis-(methylene)-cyclohexane group or a monocyclic or non-fused bicyclic aromatic radical which is unsubstituted or substituted by halogen atoms or alkyl or alkoxy groups, each with 1–4 carbon atoms.

Polyamides, polyamide-amide-acids or polyamide-acids, as well as the corresponding derivatives which have been cyclised to the imide, which consist only of structural elements of the formula VI, in which R denotes a benzene ring or an unsubstituted alkylene group with 4–10 carbon atoms when m and n=1, a benzene ring when m=1 and n=2 and a benzene ring or the benzophenone ring system when m and n=2, but especially polyamides, polyamide-amide-acids or polyamide-acids, as well as the corresponding derivatives which have been cyclised to the imide, which consist of 5–80 mol% of structural elements of the formula VI and 20–95 mol% of structural elements of the formula VII and in which m and n each denote the number 1, R denotes a benzene ring or an unsubstituted alkylene group with 4–10 carbon atoms and R$_1$ denotes an unsubstituted alkylene group with 2–12 carbon atoms, but above all the 1,3- or 1,4-phenylene group, the 4,4'-diphenylmethane radical or the 4,4'-diphenyl ether radical; m denotes the number 1 and n denotes the number 2, R denotes a benzene ring and R$_1$ denotes an unsubstituted alkylene group with 2–12 carbon atoms, but especially the 1,3- or 1,4-phenylene group, the 4,4'-diphenylmethane radical or the 4,4'-diphenyl ether radical; or m and n denote the number 2, R denotes a benzene ring or the benzophenone ring system and R$_1$ denotes an unsubstituted alkylene group with 2–12 carbon atoms, but preferably the 1,3- or 1,4-phenylene group, the 4,4'-diphenylmethane radical or the 4,4'-diphenyl ether radical, are preferred.

Polymers, according to the definition, and the corresponding derivatives which have been cyclised to the imide, which consist of 5–50 mol% of structural elements of the formula VI and 50–95 mol% of structural elements of the formula VII and in which R$_1$ denotes the 1,3-phenylene group, the 4,4'-diphenylmethane radical or the 4,4'-diphenyl ether radical, m denotes 1, n denotes 2 and R denotes a benzene ring, or m and n denote 2 and R denotes a benzene ring or the benzophenone ring system, but above all polyamide copolymers which consist of 5–50 mol% of structural elements of the formula VI and 50–95 mol% of structural elements of the formula VII and in which m and n denote the number 1, R denotes a benzene ring and $R_1$ denotes an unsubstituted alkylene group with 4–10 carbon atoms, the 1,3-phenylene group, the 4,4'-diphenylmethane radical or the 4,4'-diphenyl ether radical, are very particularly preferred.

In the abovementioned preferred polymers, the NH groups in formula VI are preferably each bonded to the benzene nucleus in the ortho-position and in particular each bonded to the benzene nucleus in the para-position.

The diamines of the formula VIII and the di-, tri- and tetra-carboxylic acid derivatives of the formula IX are known or can be manufactured according to methods which are in themselves known. Examples which may be mentioned are:

Diamines of the formula VIII o-, m- and p-Phenylenediamine, diaminotoluenes, such as 2,4-diaminotoluene, 1,4-diamino-2-methoxybenzene, 2,5-diaminoxylene, 1,3-diamino-4-chlorobenzene, 4,4'-diaminodiphenylmethane, 4,4'-diaminodiphenyl ether, 4,4'-diaminodiphenyl thioether, 4,4'-diaminodiphenylsulphone, 2,2'-diaminobenzophenone, 4,4'-diaminodiphenylurea and 1,8- or 1,5-diaminonaphthalene; 2,6-diaminopyridine, 1,4-piperazine, 2,4-diaminopyrimidine, 2,4-diamino-s-triazine, di-, tri-, tetra-, hexa-, hepta-, octa- and deca-methylenediamine, 2,2-dimethylpropylenediamine, 2,5-dimethylhexamethylenediamine, 4,4-dimethylheptamethylenediamine, 3-methylheptamethylenediamine, 3-methoxyhexamethyldiamine, 2,11-diaminododecane, 2,2,4- and 2,4,4-trimethylhexamethylenediamine, 1,2-bis-(3-aminopropoxy)ethane, N,N'-dimethylethylenediamine and N,N'-dimethyl-1,6-diaminohexane as well as the diamines of the formulae $H_2N(CH_2)_3O(CH_2)_2O(CH_2)_3NH_2$ and $H_2N(CH_2)_3S(CH_2)_3NH_2$; 1,4-diaminocyclohexane, 1,4-bis-(2-methyl-4-aminopentyl)-benzene and 1,4-bis-(aminomethyl)-benzene.

Compounds of the formula IX

Malonic acid, dimethylmalonic acid, succinic acid, glutaric acid, adipic acid, suberic acid, sebacic acid and dodecanedicarboxylic acid, 1,3-cyclopentane-dicarboxylic acid, hexahydroisophthalic acid, hexahydroterephthalic acid, terephthalic acid, isophthalic acid, 4,4'-dicarboxydiphenylethane, naphthalene-2,6-dicarboxylic acid, thiophene-2,5-dicarboxylic acid and pyridine-2,3-dicarboxylic acid as well as the corresponding dichlorides and diesters according to the definition; trimellitic acid 1,2-anhydride-chloride(1,3-dioxo-benzo[c]oxalane-5-carboxylic acid chloride), trimellitic acid anhydride and trimellitic acid as well as esters according to the definition; pyromellitic acid dianhydride, 3,3',4,4'-benzophenonetetracarboxylic acid dianhydride, 2,3,3',4'-benzophenonetetracarboxylic acid dianhydride, 2,2',3,3'-benzophenonetetracarboxylic acid dianhydride, 3,3',4,4'-diphenyl-tetracarboxylic acid dianhydride, bis-(2,3-dicarboxyphenyl)-methane dianhydride, bis-(2,5,6-trifluoro-3,4-dicarboxyphenyl)-methane dianhydride, 2,2-bis-(2,3-dicarboxyphenyl)-propane dianhydride, bis-(3,4-dicarboxyphenyl) ether dianhydride, bis-(3,4-dicarboxyphenyl)-sulphone dianhydride, N,N-(3,4-dicarboxyphenyl)-N-methylamine dianhydride, bis-(3,4-dicarboxyphenyl)-diethylsilane dianhydride, 2,3,6,7- and 1,2,5,6-naphthalene-tetracarboxylic acid dianhydride, 2,6-dichloronaphthalene-1,4,5,8-tetracarboxylic acid dianhydride, thiophene-2,3,4,5-tetracarboxylic acid dianhydride, pyrazine-2,3,5,6-tetracarboxylic acid dianhydride and pyridine-2,3,5,6-tetracarboxylic acid dianhydride.

Preferred compounds of the formula VIII are alkylenediamines with 2–12, and especially 4–10, carbon atoms and especially 1,3- or 1,4-phenylenediamine, 4,4'-diaminodiphenyl ether and 4,4'-diaminodiphenylmethane.

Acid dichlorides, acid chloride-anhydrides or dianhydrides, and especially those in which R denotes a benzene ring or the benzophenone ring system, are advantageously used as the compounds of the formula IX.

The polycondensation reaction of the compounds of the formula I with one or more compounds of the formula IX and, optionally, one or more compounds of the formula VIII is carried out in a manner which is in itself known, appropriately at temperatures of about −50° C. to +300° C. The reaction can be carried out in the melt or, preferably, in an inert organic solvent or a solvent mixture. Temperatures of −20° C. to +50° C. are preferred for the polycondensation reaction in solution.

Examples of suitable organic solvents are: chlorinated aromatic hydrocarbons, such as chlorobenzene and dichlorobenzenes, chlorinated aliphatic hydrocarbons, such as methylene chloride, chloroform, tetrachloroethane and tetrachloroethylene, aliphatic and cycloaliphatic ketones, such as acetone, methyl ethyl ketone, cyclopentanone and cyclohexanone, cyclic ethers, such as tetrahydrofurane, tetrahydropyrane and dioxane, cyclic amides, such as N-methyl-2-pyrrolidone, N-acetyl-2-pyrrolidone and N-methyl-ε-caprolactam, N,N-dialkylamides of aliphatic monocarboxylic acids with 1–3 carbon atoms in the acid part, such as N,N-dimethylformamide, N,N-dimethylacetamide, N,N-diethylacetamide and N,N-dimethylmethoxyacetamide, hexamethylphosphoric acid triamide (hexametapol), N,N,N',N'-tetramethylurea, tetrahydrothiophene dioxide (sulpholane) and dialkylsulphoxides, such as dimethylsulphoxide and diethylsulphoxide.

Preferred solvents are N,N-dialkylamides of aliphatic monocarboxylic acids with 1–3 carbon atoms in the acid part, especially N,N-dimethylacetamide, as well as cyclic amides, such as N-methyl-2-pyrrolidone.

The hydrochloric acid obtained during the condensation reaction with compounds of the formula IX in which Y represents chlorine can be removed by neutralisation with basic substances, such as calcium hydroxide or triethylamine, or by reaction with an epoxide compound, such as ethylene oxide or propylene oxide, and by washing out with suitable solvents.

The condensation reactions are appropriately carried out with the exclusion of moisture, for example in an inert gas atmosphere, such as nitrogen.

As already mentioned initially, the reaction of the di-, tri- or tetra-carboxylic acid derivatives of the formula IX with the diamines of the formula VIII and/or I can also be carried out stepwise in order to manufacture polymers which, at least in part, have a block-type distribution of the structural elements of the formula VI or VII. It is also possible to link polyamides, polyamide-amide-acids or polyamide-acids which have structural elements of the formula VI or VII and have been manufactured separately, with one another and so-called block copolymers are formed by this means. In all of these cases, the reaction is carried out in a manner which is in itself known using a slight excess of one or the other reactant in order to obtain prepolymers which have end groups suitable for the further reaction, for example amino end groups, acid chloride groups and/or anhydride groups.

The optional cyclisation of the polyamide-acids or polyamide-amide-acids (m and/or n=2) obtained after the condensation reaction is carried out in a manner which is in itself known by chemical means or by means of heat.

The chemical cyclisation is appropriately carried out by treatment with a dehydrating agent on its own or as a mixture with a tertiary amine. Reagents which can be used are, for example, acetic anhydride, propionic anhydride and dicyclohexylcarbodiimide or mixtures of acetic anhydride and triethylamine.

The cyclisation by means of heat is carried out by heating to temperatures of about 50° C. to 300° C. and preferably of about 150° C. to 250° C. and optionally with the addition of an inert organic solvent.

The polyamides, polyamide-amide-acids and polyamide-acids according to the invention, as well as the corresponding cyclised derivatives, are suitable for the manufacture of shaped articles of very diverse types, such as fibres, films, sheets, coating compositions, foams, laminating resins, composite materials, moulding powders, pressed articles and the like, in a manner which is in itself known, if desired with the use of customary additives, such as pigments, fillers and the like. The polymers according to the invention can also be processed easily from the melt and are distinguished by good mechanical, electrical and thermal properties as well as, in general, by good solubility in organic solvents, such as N,N-dimethylacetamide, N,N-dimethylformamide and N-methyl-2-pyrrolidone.

EXAMPLE 1

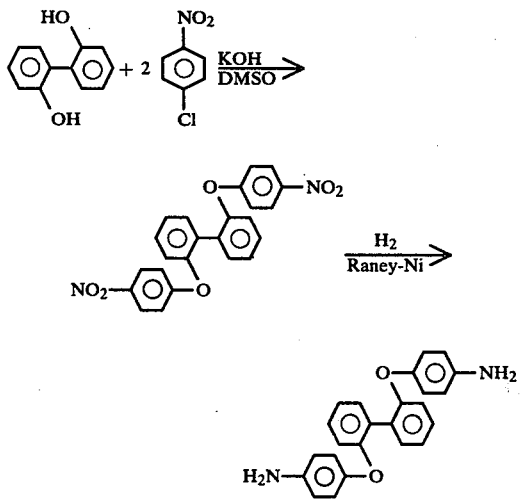

37.2 g (0.2 mol) of 2,2'-dihydroxy-biphenyl and 63 g (0.4 mol) of p-nitrochlorobenzene are dissolved in 160 ml of dimethylsulphoxide (DMSO) in a sulphonation flask and the solution is warmed to 80° C. A solution of 26.4 g (0.4 mol) of 85% strength potassium hydroxide in 20 ml of water is then added dropwise, whilst stirring, and the reaction solution is subsequently further stirred for 3 hours at 100°-110° C. After cooling, the reaction solution is poured into ice water and the resulting precipitate is washed several times with water. The resulting crude product is then dried for 20 hours under a high vacuum at 70° C. and unconverted nitrochlorobenzene sublimes away during drying. The residue is recrystallised twice from ethanol. 12.4 g (15% of theory) of 2,2'-di-(p-nitrophenoxy)-biphenyl are obtained in the form of slightly yellowish crystals; melting point 158° C.

| Analysis for $C_{24}H_{16}O_6N_2$ (molecular weight 428.41): | | | |
|---|---|---|---|
| calculated | C 67.3% | H 3.72% | N 6.55% |
| found | C 67.1% | H 3.8% | N 6.4%. |

82.5 g of the above 2,2'-di-(p-nitrophenoxy)-biphenyl are hydrogenated with 24 g of Raney nickel in 900 ml of dioxane at 40°-50° C. After filtering off the catalyst and evaporating the solvent, 70 g (99% of theory) of crude 2,2'-di-(p-aminophenoxy)-biphenyl are obtained and this is recrystallised twice from ethanol. After recrystallisation, 51.6 g (73% of theory) of pure 2,2'-d-(p-aminophenoxy)-biphenyl are obtained in the form of slightly yellowish crystals; melting point 158° C.

| Analysis for $C_{24}H_{20}O_2N_2$ (molecular weight 368.44): | | | |
|---|---|---|---|
| calculated | C 78.24% | H 5.47% | N 7.61% |
| found | C 78.1% | H 5.6% | N 7.6%. |

EXAMPLE 2

74.4 g (0.4 mol) of 2,2'-dihydroxy-biphenyl are suspended in 400 ml of distilled water in a round-bottomed flask and 53.5 g (0.8 mol) of 84% pure solid potassium hydroxide are then added in portions at 20°-25° C., whilst stirring. The reaction mixture is stirred further until all of the 2,2'-dihydroxy-biphenyl has dissolved. The reaction solution is then evaporated to dryness in a rotary evaporator. 315 g (2 mols) of p-nitrochlorobenzene are added to the residue (the dipotassium salt of 2,2'-dihydroxy-biphenyl), the round-bottomed flask is provided with a riser and the reaction mixture is heated to 150° C. for 2 hours, whilst stirring. After cooling to about 100° C., the resulting melt is poured into 2 liters of chloroform. The resulting solution is extracted twice with water, dried over potassium carbonate and evaporated in a rotary evaporator. In order to remove excess p-nitrochlorobenzene, the residue is suspended in 2 liters of diethyl ether and the suspended is warmed under reflux for a short time. The reaction mixture is then filtered and the material on the filter is rinsed with diethyl ether and, after decolourising with active charcoal, the product is recrystallised from ethanol. This gives 38.9 g (23% of theory) of the 2,2'-di-(p-nitrophenoxy)-biphenyl (of analytical purity) characterised in Example 1.

The hydrogenation to 2,2'-di-(p-aminophenoxy)-biphenyl is carried out as described in Example 1.

EXAMPLE 3

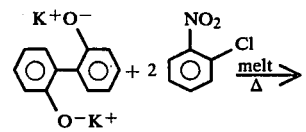

-continued

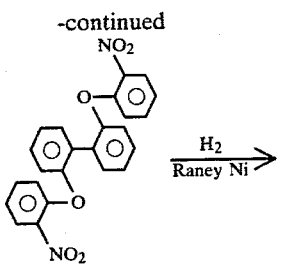

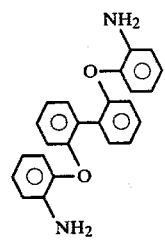

Analogously to the procedure described in Example 2, 37.2 g (0.2 mol) of 2,2'-dihydroxy-biphenyl are converted into the corresponding dipotassium salt using 26.8 g (0.4 mol) of 84% pure solid potassium hydroxide in 200 ml of water. This salt is reacted in the melt with 157 g (1 mol) of o-chloronitrobenzene, in the manner described in Example 2. The crude product which is obtained after removal of the chloroform is dissolved hot in methanol, the solution is decolourised with active charcoal and the product is crystallised. The product is then recrystallised once more from ethanol and 20.3 g (24% of theory) of 2,2'-di-(o-nitrophenoxy)-biphenyl are obtained in the form of pale yellowish crystals; melting point 154° C.

| Analysis for $C_{24}H_{16}O_6N_2$ (molecular weight 428.41): | | | |
|---|---|---|---|
| calculated | C 67.3% | H 3.72% | N 6.55% |
| found | C 67.3% | H 3.8% | N 6.5%. |

27 g of 2,2'-di-(o-nitrophenoxy)-biphenyl are hydrogenated with 3 g of Raney nickel in 270 ml of dioxane at 35°–40° C. After filtering off the catalyst and evaporating the solvent, 23 g (99% of theory) of crude diamine results and this is recrystallised twice from ethanol. This gives 16.2 g (70% of theory) of 2,2'-di-(o-aminophenoxy)-biphenyl in the form of colourless crystals; melting point 175° C.

| Analysis for $C_{24}H_{20}O_2N_2$ (molecular weight 368.44): | | | |
|---|---|---|---|
| calculated | C 78.25% | H 5.47% | N 7.61% |
| found | C 78.28% | H 5.53% | N 7.66%. |

EXAMPLE 4

Analogously to the procedure described in Example 1, 74.4 g (0.4 mol) of 2,2'-dihydroxy-biphenyl, 126 g (0.8 mol) of o-nitrochlorobenzene, 52.8 g (0.8 mol) of 85% pure solid potassium hydroxide and 40 ml of water are reacted in 200 ml of dimethylsulphoxide. After recrystallising the crude product twice from ethanol, 11.49 g (7% of theory) of the 2,2'-di-(o-nitrophenoxy)-biphenyl characterised in Example 3 are obtained. The hydrogenation to 2,2'-di-(o-aminophenoxy)-biphenyl is carried out as described in Example 3.

EXAMPLE 5

18.62 g (0.1 mol) of 2,2'-dihydroxy-biphenyl and 28.22 g (0.2 mol) of p-nitrofluorobenzene are dissolved in 80 ml of dimethylsulphoxide in a sulphonation flask and the solution is warmed to 80° C. A solution of 13.2 g (0.2 mol) of 85% pure potassium hydroxide in 10 ml of water is then added dropwise, whilst stirring, and the reaction solution is subsequently further stirred for 3 hours at 100°–110° C. During this time a yellow precipitate forms and after the reaction mixture has cooled this is separated off by decanting off the supernatant liquor and is then washed several times with water. After drying, the crude product is recrystallised from ethanol. 32.86 g (77% of theory) of 2,2'-di-(p-nitrophenoxy)-biphenyl of analytical purity are obtained in the form of slightly yellowish crystals with a melting point of 158° C.

Hydrogenation of the above product by the method described in Example 1 and recrystallisation of the resulting crude product from ethanol gives 2,2'-di-(p-aminophenoxy)-biphenyl which is of analytical purity and has a melting point of 157°–158° C.

EXAMPLE 6

18.62 g (0.1 mol) of 2,2'-dihydroxydiphenyl, 28.22 g (0.2 mol) of o-nitrofluorobenzene, 13.2 g (0.2 mol) of 85% pure solid potassium hydroxide and 10 ml of water are reacted in 80 ml of dimethylsulphoxide according to the procedure described in Example 5. After washing and recrystallising the resulting precipitate, 28.82 g (67% of theory) of 2,2'-di-(o-nitrophenoxy)-biphenyl of analytical purity are obtained in the form of slightly yellowish crystals with a melting point of 153°–154° C.

Hydrogenation of the above product by the procedure described in Example 3 and recrystallisation of the crude product from ethanol gives 2,2'-di(o-aminophenoxy)-biphenyl which is of analytical purity and has a melting point of 174°–175° C.

EXAMPLE 7

18.62 g (0.1 mol) of 2,2'-dihydroxybiphenyl, 14.11 g (0.1 mol) of p-nitrofluorobenzene, 14.11 g (0.1 mol) of o-nitrofluorobenzene, 13.2 g (0.2 mol) of 85% pure solid potassium hydroxide and 10 ml of water are reacted in 80 ml of dimethylsulphoxide according to the procedure described in Example 5. After cooling, the reaction solution is poured into water and the precipitate formed is washed several times with water and dried in a vacuum drying cabinet at 80° C. for 16 hours. The crude product is then dissolved in hot ethanol and the resulting solution is cooled with an ice bath, whilst stirring intensively. A fine, slightly yellowish powder precipitates out and this is filtered off and dried. This gives 19.3 g (45% of theory) of a mixture of isomers (melting point 92°–118° C.) which, according to the thin layer chromatogram, contains the three isomers 2,2'-di-(o-nitrophenoxy)-biphenyl, 2,2'-di-(p-nitrophenoxy)-biphenyl and 2-(p-nitrophenoxy)-2'-(o-nitrophenoxy)-biphenyl in a weight ratio of 1:1:1.

The above mixture of isomers is hydrogenated according to the procedure described in Example 1. The resulting crude product is separated into the individual isomers by column chromatography over silica gel. In addition to the diamines described in Examples 5 and 6, 2-(p-aminophenoxy)-2'-(o-aminophenoxy)-biphenyl which is of analytical purity and has a melting point of 162°–163° C. is obtained.

EXAMPLE 8

5.526 g (0.015 mol) of the 2,2'-di-(p-aminophenoxy)-biphenyl prepared according to Example 1 are dissolved in 90 ml of anhydrous N,N-dimethylacetamide (DMA) in a sulphonation flask, under a nitrogen atmosphere, and the solution is cooled to 0°–5° C. 4.83 g (0.015 mol) of 3,3',4,4'-benzophenonetetracarboxylic acid dianhydride in solid form are added in portions to this solution, whilst stirring. The resulting viscous solution is then stirred for a further 30 minutes at 0°–5° C. and subsequently for a further 2 hours at 20°–25° C. The intrinsic viscosity of the polyamide-acid thus formed is 0.75 dl/g (0.5% by weight in DMA at 25° C.).

Part of this polyamide-acid solution is spread to give a film. The film is dried in vacuo as follows: 1 hour at 60° C., 1 hour at 100° C., 1 hour at 150° C. and 16 hours at 200° C. A transparent, flexible film is obtained.

A mixture of 45 ml of acetic anhydride and 30 ml of pyridine is added dropwise to the remainder of the above polyamide-acid solution. Subsequently, the reaction mixture is stirred for 16 hours at 20°–25° C. and then poured into water. The precipitate thus formed is washed several times with water and dried in a vacuum drying cabinet for 20 hours at 150° C./20 mm Hg and for 20 hours at 200° C./0.1 mm Hg. 7.8 g of polyimide in the form of a yellow powder are obtained.

For processing by the compression moulding process, the above polyimide is introduced into a compression mould for circular sheets, which has been prewarmed to 320° C., and compression moulded at this temperature for 3 minutes under the contact pressure and for 5 minutes under a pressure of 225 kp/cm². Strong, transparent mouldings which have good mechanical and electrical properties even at elevated temperatures are obtained.

EXAMPLE 9

Analogously to the procedure described in Example 8, 1.842 g (0.005 mol) of the 2,2'-di-(o-aminophenoxy)-biphenyl prepared according to Example 3, in 37 ml of anhydrous DMA, are reacted with 1.611 g (0.005 mol) of 3,3',4,4'-benzophenonetetracarboxylic acid dianhydride. The resulting polyamide-acid has an intrinsic viscosity of 0.20 dl/g (0.5% by weight in DMA at 25° C.).

EXAMPLE 10

3.68 g (0.01 mol) of 2,2'-di-(p-aminophenoxy)-biphenyl are dissolved in 50 ml of anhydrous DMA in a sulphonation flask, under a nitrogen atmosphere, and the solution is cooled to −15° C. 2.03 g (0.01 mol) of isophthalic acid dichloride in the solid form are then added in portions, whilst stirring, in such a way that the temperature of the reaction mixture does not rise above −5° C. The reaction mixture is then rinsed with 10 ml of DMA and stirred for a further 1 hour at −5° C. and then for a further 1 hour at 20°–25° C. Finally, the reaction mixture is cooled and a solution of 2.02 g (0.02 mol) of triethylamine in 10 ml of DMA is added dropwise at −5° C. After stirring for 1 hour at 20°–25° C., the triethylamine hydrochloride which has precipitated is filtered off.

Part of the resulting polyamide solution is cast to give a film and the film is dried in a vacuum oven for 1 hour at 60° C., for 1 hour at 100° C. and for 16 hours at 150° C. A transparent film is obtained.

The remainder of the polyamide solution is poured into water. Thereupon, the polyamide precipitates in the form of a powder and this is dried in vacuo at 150° C. The polyamide is soluble in DMA and is pressed in a platen press at 260° C. to give small, transparent, flexible sheets.

EXAMPLE 11

2.210 g (0.006 mol) of 2,2'-di-(p-aminophenoxy)-biphenyl and 2.804 g (0.014 mol) of 4,4'-diaminodiphenyl ether are dissolved in 100 ml of anhydrous DMA in a sulphonation flask, under a nitrogen atmosphere, and the solution is cooled to 15° C. 6.445 g (0.02 mol) of 3,3',4,4'-benzophenonetetracarboxylic acid dianhydride in the solid form are then added in portions and the reaction mixture is stirred for 1 hour at 15° C. and then for 2 hours at 20°–25° C.

Part of the resulting highly viscous polyamide-acid solution is spread on a glass plate to give a film and the film is dried in a vacuum drying cabinet for 1 hour at 60° C., for 1 hour at 100° C. and for 16 hours at 200° C. A transparent flexible film with good mechanical properties is obtained.

A mixture of 90 ml of acetic anhydride and 60 ml of pyridine is added dropwise to the remainder of the above polyamide-acid solution and the reaction mixture is stirred for 16 hours at 20°–25° C. The reaction mixture is then poured into water. The copolyimide which has precipitated is washed with water and dried for 20 hours at 120° C. and for 20 hours at 200° C. in a vacuum drying cabinet. The polymer has an intrinsic viscosity of 0.48 dl/g (0.5% by weight in concentrated $H_2SO_4$ at 25° C.). Pressing in a platen press at 320° C. gives transparent flexible sheets with good mechanical properties.

At 320° C., it was not possible to press a known polyimide, which was prepared by the process described above from 4,4'-diaminodiphenyl ether and 3,3',4,4'-benzophenonetetracarboxylic acid dianhydride (molar ratio 1:1), to flexible sheets.

EXAMPLE 12

In accordance with the procedure described in Example 11, 2.947 g (0.008 mol) of 2,2'-di-(p-aminophenoxy)-biphenyl in 110 ml of anhydrous DMA are reacted with 2.37 g (0.012 mol) of 4,4'-diaminodiphenylmethane and 6.445 g (0.02 mol) of 3,3',4,4'-benzophenonetetracarboxylic acid dianhydride and the resulting polyamide-acid is processed to give films and a polyimide powder. The films are transparent, tough and flexible. The powder has an intrinsic viscosity of 0.4 dl/g (0.5% by weight in concentrated $H_2SO_4$ at 25° C.) and can be pressed at 280° C. in a platen press to give transparent flexible sheets.

EXAMPLE 13

In accordance with the procedure described in Example 11, 2.210 g (0.006 mol) of 2,2'-di-(o-aminophenoxy)-biphenyl in 110 ml of anhydrous DMA are reacted with 2.804 g (0.014 mol) of 4,4'-diaminodiphenyl ether and 6.445 g (0.02 mol) of 3,3',4,4'-benzophenonetetracarboxylic acid dianhydride. The resulting polyamide-acid is processed to give a powder. The copolyimide has an intrinsic viscosity of 0.37 dl/g (0.5% by weight in concentrated $H_2SO_4$ at 25° C.) and can be pressed to transparent sheets at 260° C. in a platen press.

EXAMPLE 4

In accordance with the procedure described in Example 11, 1.84 g (0.005 mol) of 2,2'-di-(p-aminophenoxy)-biphenyl are reacted with 4.00 g (0.02 mol) of 4,4'-diaminodiphenyl ether and 5.45 g (0.025 mol) of pyromellitic acid dianhydride in 160 ml of anhydrous DMA and the copolyamide-acid is processed to give transparent flexible films.

EXAMPLE 15

3.68 g (0.01 mol) of 2,2'-di-(p-aminophenoxy)-biphenyl and 7.93 g (0.04 mol) of 4,4'-diaminodiphenylmethane are dissolved in 110 ml of anhydrous DMA in a sulphonation flask, under a nitrogen atmosphere, and the solution is cooled to $-20°$ C. 10.53 g (0.05 mol) of trimellitic acid anhydride-chloride in the solid form are then added, whilst stirring, and the reaction solution is stirred for 15 minutes at $-20°$ C. and then for 2 hours at $20°-25°$ C. Subsequently, the reaction solution is cooled again and a solution of 10.22 g (0.10 mol) of triethylamine in 20 ml of DMA is then added dropwise at $-15°$ C. After stirring for 2 hours at $20°-25°$ C., the triethylamine hydrochloride which has precipitated is filtered off. 60 ml of acetic anhydride are added dropwise to the filtrate. The reaction mixture is stirred for a further 16 hours at $20°-25°$ C. and is then poured into water. The copolyamide-imide which has precipitated is washed with water and ethanol and dried for 24 hours at $200°$ C./0.1 mm Hg. This gives 18.24 g of the copolyamide-imide in the form of a yellow powder which is soluble in dimethylacetamide.

For processing by the compression moulding process, the powder is introduced into a compression mould for standard bars, which has been preheated to $300°$ C., and compression moulded at this temperature for 5 minutes under a pressure of 500 kp/cm$^2$. Transparent strong mouldings with good mechanical properties are obtained.

EXAMPLE 16

7.37 g (0.02 mol) of 2,2'-di-(p-aminophenoxy)-biphenyl and 19.46 g (0.18 mol) of m-phenylenediamine are dissolved in 350 ml of anhydrous DMA in a sulphonation flask, under a nitrogen atmosphere, and the solution is cooled to $-20°$ C. 40.6 g (0.2 mol) of isophthalic acid dichloride in the solid form are then added, whilst stirring. The reaction mixture is stirred for a further 15 minutes at $-20°$ C. and then for a further 2 hours at $20°-25°$ C. and cooled again and a solution of 40.47 g (0.4 mol) of triethylamine in 55 ml of DMA is added dropwise at $-15°$ C. The reaction mixture is again stirred for 2 hours at $20°-25°$ C. The resulting highly viscous reaction mixture is then diluted with 300 ml of DMA. The triethylamine hydrochloride which has precipitated is filtered off. The reaction solution is poured into water. The copolyamide which has precipitated is washed with water and ethanol and dried for 4 hours at $150°$ C./20 mmHg $200°$ C./0.1 mm Hg. This gives 48 g of copolyamide, which is soluble in dimethylacetamide. The intrinsic viscosity is 1.24 dl/g (0.5% by weight in DMA at $25°$ C.) and the glass transition temperature is $266°$ C.

A 20% strength solution of this copolyamide in N,N-dimethylacetamide is cast to give films and the films are dried as follows: 3 hours at $80°$ C./20 mm Hg, 1 hour at $150°$ C./0.1 mm Hg and 16 hours at $250°$ C./0.1 mm Hg. Tough, transparent flexible films are obtained.

For processing by the compression moulding process, the copolyamide is introduced into a compression mould which has been preheated to $320°$ C. and compression moulded at this temperature for 3 minutes under the contact pressure and for 5 minutes under a pressure of 500 kp/cm$^2$. Transparent, firm bars or sheets which have excellent mechanical and electrical properties (flexural strength 231 N/mm$^2$, modulus of elasticity 4,000 N/mm$^2$) are obtained. In comparison with this, a homopolyamide obtained from m-phenylenediamine and isophthalic acid dichloride from the melt cannot be compression moulded to give shaped articles. Moreover, it is soluble in dimethylacetamide only when lithium chloride is added.

EXAMPLE 17

In accordance with the procedure described in Example 16, 14.74 g (0.04 mol) of 2,2'-di-(p-aminophenoxy)-biphenyl in 440 ml of anhydrous DMA are reacted, in the presence of 40.47 g (0.4 mol) of triethylamine with 17.30 g (0.16 mol) of m-phenylenediamine and 40.6 g (0.2 mol) of isophthalic acid dichloride and the polymer is precipitated. This gives 54 g of copolyamide, which is soluble in DMA. The intrinsic viscosity is 1.11 dl/g (0.5% by weight in DMA at $25°$ C.) and the glass transition temperature is $260°$ C. (determined by DSC=Differential Scanning Calorimetry).

A 20% strength solution of this copolyamide in N,N-dimethylacetamide is processed to films in accordance with Example 16. Transparent flexible films with very good mechanical and electrical properties are obtained.

Part of the copolyamide is also processed according to Example 16 by the compression moulding process to transparent shaped articles which have good stability to heat and good mechanical properties.

EXAMPLE 18

In accordance with Example 16, 22.11 g (0.06 mol) of 2,2'-di-(p-aminophenoxy)-biphenyl, 15.14 g (0.14 mol) of m-phenylenediamine, 40.6 g (0.2 mol) of isophthalic acid dichloride and 40.47 g (0.4 mol) of triethylamine are reacted in 470 ml of anhydrous DMA. The resulting copolyamide is processed to give a powder. The copolyamide is soluble in DMA; intrinsic viscosity 1.03 dl/g (0.5% by weight in DMA at $25°$ C.).

A 20% strength solution of this copolyamide in N,N-dimethylacetamide is processed according to Example 16 to give transparent flexible films. The films have good stability to thermo-oxidation and good mechanical properties.

EXAMPLE 19

In accordance with Example 16, 3.68 g (0.01 mol) of 2,2'-di-(p-amino-phenoxy)-biphenyl, 20.55 g (0.19 mol) of m-phenylenediamine, 40.6 L g (0.20 mol) of isophthalic acid dichloride and 40.76 L g (0.4 mol) of triethylamine are reacted in 390 ml of anhydrous DMA. The resulting copolyamide (47 g) is processed to a powder; intrinsic viscosity 1.01 dl/g (0.5% by weight in DMA at $25°$ C.).

A 20% strength solution of the copolyamide in DMA is processed to give transparent flexible films which have good mechanical properties and good stability to thermo-oxidation.

Compression moulding of the copolyamide by the compression moulding process at $320°$ C., as described in Example 16, gives strong mouldings which have good mechanical and electrical properties.

EXAMPLE 20

In accordance with Example 16, 1.47 g (0.004 mol) of 2,2'-di-(o-aminophenoxy)-biphenyl, 3.89 g (0.036 mol) of m-phenylenediamine, 8.12 g (0.04 mol) of isophthalic acid dichloride and 8.09 g (0.08 mol) of triethylamine are reacted in 80 ml of anhydrous DMA. The resulting copolyamide is processed to a powder. This gives 9.6 g of copolyamide, which is soluble in DMA. The intrinsic viscosity is 0.4 dl/g (0.5% by weight in DMA at 25° C.).

The copolyamide is compression moulded by the compression moulding process at 320° C., in accordance with the procedure described in Example 16, to give strong mouldings which have good electrical properties.

EXAMPLE 21

In accordance with the procedure described in Example 10, 3.68 g (0.01 mol) of 2,2'-di-(p-aminophenoxy)-biphenyl, 1.16 g (0.01 mol) of hexamethylenediamine, 4.06 g (0.02 mol) of terephthalic acid dichloride and 4.04 g (0.04 mol) of triethylamine are reacted in 40 ml of anhydrous DMA. The reaction solution is then poured into water. The product which has precipitated is washed and dried and then pressed in a platen press at 280° C. to give transparent sheets.

EXAMPLE 22

In accordance with the procedure described in Example 10, 5.89 g (0.016 mol) of 2,2'-di-(p-aminophenoxy)-biphenyl, 0.80 g (0.004 mol) of 4,4'-diaminodiphenyl ether, 4.78 g (0.02 mol) of sebacic acid dichloride and 4.05 g (0.04 mol) of triethylamine are reacted in 50 ml of anhydrous DMA. Part of the resulting polyamide solution is cast to give a film and the film is dried in a drying cabinet for 16 hours at 70° C./20 mm Hg, for 1 hour at 100° C./0.1 mm Hg, for 1 hour at 150° C./0.1 mm Hg and for 1 hour at 200° C./0.1 mm Hg and also for 2 hours at 250° C./0.1 mm Hg. Very flexible films are obtained.

The remainder of the polyamide solution is poured into water. The polyamide which has precipitated is then dried in vacuo at 80° C. and pressed in a platen press at 200° C. to give transparent, very flexible small sheets.

What is claimed is:

1. A diamine of the formula

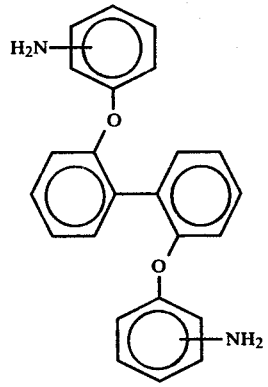

in which the two amino groups independently of one another are in the o-, m- or p-position of the benzene ring.

2. A diamine of the formula (I) according to claim 1, in which the two amino groups are each in the ortho-position or para-position of the benzene ring.

3. A diamine according to claim 1 which is 2,2'-di-(p-aminophenoxy)biphenyl.

4. A diamine according to claim 1 which is 2,2'-di-(o-aminophenoxy)-biphenyl.

5. A diamine according to claim 1 which is 2-(p-aminophenoxy)-2'-(o-aminophenoxy)-biphenyl.